United States Patent [19]

Nabi et al.

[11] Patent Number: 5,275,805
[45] Date of Patent: Jan. 4, 1994

[54] ORAL COMPOSITION CONTAINING SALICYLANILIDE ANTIBACTERIAL AGENT

[76] Inventors: Nuran Nabi, 3 Bradley Ct., North Brunswick, N.J. 08902; Abdul Gaffar, 89 Carter Rd., Princeton, N.J. 08548; John Afflitto, 2 Jay Dr., Brookside, N.J. 07926

[21] Appl. No.: 75,255

[22] Filed: Jun. 11, 1993

[51] Int. Cl.$^5$ .......................... A61K 7/16; A61K 7/22
[52] U.S. Cl. .......................................... 424/54; 424/49
[58] Field of Search ........................... 424/49–

[56] References Cited

U.S. PATENT DOCUMENTS

| | | | |
|---|---|---|---|
| 3,762,859 | 10/1973 | Wixon et al. | 8/680 |
| 3,897,548 | 7/1975 | Katz | 424/54 |
| 4,022,880 | 5/1977 | Vinson et al. | 424/54 |
| 4,100,269 | 7/1978 | Pader | 424/54 |
| 4,205,061 | 5/1980 | Vidra | 424/55 |
| 4,239,631 | 12/1980 | Brown | 252/8.75 |
| 4,323,466 | 4/1982 | Curry et al. | 252/106 |
| 4,358,466 | 4/1982 | Coburn et al. | 514/166 |
| 4,749,562 | 6/1988 | Lane et al. | 424/49 |
| 4,828,849 | 5/1989 | Lynch et al. | 424/52 |
| 4,975,217 | 12/1990 | Brown-Skrobot | 252/107 |
| 5,135,738 | 8/1992 | Gaffar et al. | 424/49 |
| 5,167,951 | 12/1992 | Gaffar et al. | 424/49 |
| 5,219,887 | 6/1993 | Andrews et al. | 514/552 |

*Primary Examiner*—Shep K. Rose
*Attorney, Agent, or Firm*—Paul Shapiro; Robert C. Sullivan

[57] ABSTRACT

An antiplaque oral composition such as a gel, paste or mouthrinse which is comprised of a vehicle having incorporated therein as the antiplaque agent an effective amount of an antibacterial salicylanilide compound and a surfactant mixture of an anionic surfactant, a polyoxyethylene/polyoxypropylene block copolymer and a taurate salt, the pH of the composition being adjusted to a pH of at least 8.0. An antibacterial-enhancing agent such as an anionic polymeric polycarboxylate which enhances the delivery of the salicylanilide compound to and retention on oral tissue surfaces is optionally incorporated in the composition to improve the efficacy of the salicylanilide compound.

30 Claims, No Drawings

ORAL COMPOSITION CONTAINING SALICYLANILIDE ANTIBACTERIAL AGENT

BACKGROUND OF THE INVENTION

1. Field of the Invention

This invention relates to an antibacterial, antiplaque oral composition. More particularly, it relates to an oral composition containing a substantially water insoluble salicylanilide antibacterial agent effective to inhibit plaque and more particularly to an oral composition containing a halogenated salicylanilide antibacterial agent wherein the oral composition exhibits a reduced tendency to undergo phase separation and exhibits improved antiplaque efficacy.

2. The Prior Art

Dental plaque is a soft deposit which forms on teeth as opposed to calculus which is a hard calcified deposit on teeth. Unlike calculus, plaque may form on any part of the tooth surface, particularly including at the gingival margin. Besides being unsightly, it is implicated in the occurrence of gingivitis.

Salicylanilide compounds have been identified by the art to be effective antiseptics against microorganisms prevalent in dental plaque. For example U.S. Pat. Nos. 4,287,191, 4,358,443 and 4,939,132 disclose that certain salicylanilide compounds such as 5-acylsalicylanilides, 5-alkyl salicylanilides and 5-alkylsulfonyl salicylanilides are highly effective against bacteria prevalent in plaque, including S. mutans. U.S. Pat. Nos. 5,154,917, 5,145,667, and 4,749,562 disclose that halogenated salicylanilide compounds are effective antiplaque agents.

Accordingly, it is highly desirable to include salicylanilide compounds in oral compositions such as toothpastes, gels and mouthrinses. However the salicylanilide compounds are water insoluble and extremely hydrophobic and are incompatible with most conventional oral compositions which are aqueous based formulations containing anionic surfactants such as sodium lauryl sulfate. It has therefore been observed that when aqueous based oral compositions are prepared using a salicylanilide antibacterial agent such as a 5-acylsalicylanilide, there is a tendency for the oral composition to be unstable and separate into two distinct phases either liquid/solid portions or liquid/liquid portions, rendering the oral composition undesirable for use by consumers. When attempts are made to formulate stable oral care products with the salicylanilide compound using a variety of nonionic surfactants it has been determined that the antibacterial efficacy of the compound is compromised.

There is therefore a need in the art to provide oral compositions containing salicylanilide compounds effective for antiplaque activity wherein phase separation of the dentifrice is substantially avoided without compromise of the efficacy of the compound.

SUMMARY OF THE INVENTION

In accordance with certain of its aspects, this invention relates to an oral composition containing a salicylanilide antibacterial agent in an amount effective to reduce plaque in the oral cavity, the composition comprising an aqueous vehicle having incorporated therein the salicylanilide compound and a surfactant admixture of an anionic surfactant, a taurate salt and a polyoxymer, the surfactant admixture being effective to stabilize the oral composition to phase separation without compromise of the antibacterial efficacy of the salicylanilide compound.

DESCRIPTION OF THE PREFERRED EMBODIMENTS

The salicylanilide compounds useful in the practice of the present invention include the following compounds:

(1) 5-acylsalicylanilides of the formula:

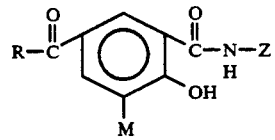

Where Z is a substituted phenyl ring of from 6 to 30 carbon atoms including substituents, R is a substituted or unsubstituted alkyl or phenyl group of from 2 to 30 carbon atoms including substituents and M is a radical selected from the group consisting of —C—N—, —F—, —NO$_2$, —H, lower alkyl or lower haloalkyl.

(2) 5-alkylsalicylanides of the formula:

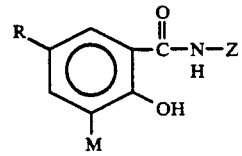

Where Z is a substituted phenyl ring of from 6 to 30 carbon atoms including substituents, and R is a substituted or unsubstituted n-alkyl or phenyl group of from 4 to 30 carbon atoms including substituents.

(3) 5-alkylsulfonylsalicylanilides of the formula:

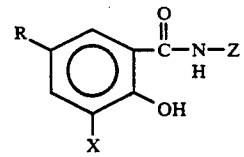

Wherein Z is a substituted or unsubstituted phenyl ring of from 6 to 30 carbon atoms including substituents; R is a substituted or unsubstituted alkylsulfonyl group of from 1 to 20 carbon atoms including substituents; and X is a radical selected from the group consisting of —CN, —NO$_2$, —H, halogen, lower alkyl or lower halo-alkyl.

(4) Halogenated salicylanilides such as:
5-dibromosalicylanilide
3,4′,5-trichlorosalicylanilide
3,4′,5-tribromosalicylanilide
2,3,3′,5-tetrachlorosalicylanilide
3,3,3′,5-tetrachlorosalicylanilide
3,5-dibromo-3′-trifluromethyl salicylanilide
3,5-dibromo-4′-trifluoromethyl salicylanilide
3,5-dibromo-3′-trifluro methyl salicylanilide.

A preferred salicylanilide compound for use in the practice of the present invention is 5-n-octanoyl-3′-trifluoromethyl salicylanilide having the formula:

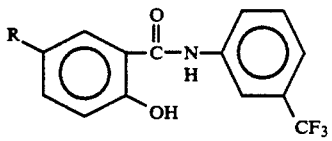

where R is $CH_3(CH_2)_8C-$.

In preparing the antibacterial oral compositions of the present invention, the salicylanilide compound is present in the oral composition in an effective antiplaque amount typically about 0.005% to about 1% by weight, preferably about 0.02% to about 1.0% by weight.

It is a critical feature of the present invention that in order to obtain oral compositions which are stable and exhibit effective antibacterial activity there must be incorporated in combination with the salicylanilide compound a surfactant system based on a combination of the following surfactants: (1) an anionic surfactant such as sodium lauryl sulfate, (2) a nonionic polyoxymer such as a polyoxyethylene/polypropylene block copolymer and (3) a taurate salt.

The surfactant combination is incorporated in the oral compositions of the present invention in an amount of about 0.2 to about 3.0% by weight and preferably about 0.5 to about 2.0% by weight. When incorporating the surfactant system in the oral compositions of the present invention the weight ratio of anionic surfactant: polyoxymer: taurate salt is about 1:2:1 to 4:1:4. A weight ratio of about 1:1:1 is preferred.

Suitable examples of anionic surfactants are water-soluble salts of higher fatty acid monoglyceride monosulfates, such as the sodium salt of the monosulfated monoglyceride of hydrogenated coconut oil fatty acids, higher ($C_8-C_{22}$) alkyl sulfates such as sodium lauryl sulfate, alkyl aryl sulfonates such as sodium dodecyl benzene sulfonate, higher alkyl sulfoacetates such as $C_{10}-C_{18}$ sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine and the sodium, potassium, and ethanolamine salts of N-lauroyl, N-myristoyl, or N-palmitoyl sarcosine. Sodium lauryl sulfate is a preferred anionic surfactant for use in the practice of the present invention.

Examples of polyoxymers useful in the practice of the present invention include block copolymers of polyoxyethylene and polyoxypropylene having an average molecular weight from about 3000 to 5000 and a preferred average molecular weight from about 3500 to about 4000 and containing about 10-80% hydrophilic polyoxyethylene groups, by weight, of the block copolymer. A preferred polyoxmer useful in the practice of the present invention is Pluronic F127 (trademark) a block copolymer of polyoxyethylene and polyoxypropylene having a molecular weight of about 4000.

Taurate salts useful as surfactants in the practice of the present invention include fatty acid esters of alkali methyl taurates such as sodium methyl cocoyl taurate, sodium methyl oleoyl taurate and sodium methyl palmitoyltaurate. Sodium methyl cocoyl taurate available under the trademark Tauranol is preferred for use in the practice of the present invention.

It is also critical to the practice of the present invention that the pH of the oral composition be in the alkaline range and be at least pH 8.0. At a pH less than 8.0 the stability and antibacterial efficacy of the salicylanilide compound is found to be substantially diminished. A pH of about 8.4 to 8.8 is preferred in the practice of the present invention, a pH of 8.6 being especially preferred.

To enhance substantibity and increase the antibacterial activity of the salicylanilide compound, an antibacterial enhancing agent is included in the oral composition. The use of antibacterial enhancing agents in combination with water-insoluble antibacterial compounds is known to the art, as for example U.S. Pat. No. 5,188,821 and 5,192,531. An antibacterial enhancing agent is an organic material which contains a delivery-enhancing group and a retention-enhancing group. As employed herein, the delivery-enhancing group refers to one which attaches or substantially, adhesively, cohesively or otherwise bonds the antibacterial enhancing agent (carrying the salicylanilide compound) to oral (e.g. tooth and gum) surfaces, thereby "delivering" the salicylanilide compound to such surfaces. The organic retention-enhancing group, generally hydrophobic, attaches or otherwise bonds the salicylanilide compound to the antibacterial enhancing agent, thereby promoting retention of the salicylanilide compound to the antibacterial enhancing agent and indirectly on the oral surfaces. The enhances retention of the salicylanilide on the oral surfaces results in an improvement in the retardation of plaque growth on oral surfaces.

Preferably, the antibacterial enhancing agent is an anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain.

The antibacterial enhancing agent may be a simple compound, preferably a polymerizable monomer, more preferably a polymer, including for example oligomers, homopolymers, copolymers of two or more monomers, ionomers, block copolymers, graft copolymers, cross-linked polymers and copolymers, and the like. The antibacterial enhancing agent may be natural or synthetic, and water insoluble or preferably water (saliva) soluble or swellable (hydratable, hydrogel forming) having an average molecular weight of about 100 to about 1,000,000, preferably about 1,000 to about 1,000,000, more preferably about 25,000 to 500,000.

In the case of the polymeric antibacterial enhancing agents, it is desirable, for maximizing delivery and retention of the salicylanilide compound to oral surfaces, that the repeating units in the polymer chain or backbone containing the acidic delivery enhancing groups constitute at least about 10%, preferably at least about 50%, more preferably at least about 80% up to 95% or 100% by weight of the polymer.

The antibacterial enhancing agent generally contains at least one delivery-enhancing group, which is preferably acidic such as sulfonic, phosphonic, or more preferably phosphonic or carboxylic, or a salt thereof, e.g. alkali metal or ammonium and at least one organic retention-enhancing group, such groups having the formula $-(X)_n-R$ wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired function of the antibacterial enhancing agent as enhancing the delivery of the salicylanilide compound to and retention thereof on oral surfaces such as halo, e.g. Cl, Br, I, and carbo and the like. Illustrations of such retention-enhancing groups are tabulated below.

| n | X | —(X)n$^R$ |
|---|---|---|
| 0 | | methyl, ethyl, propyl, butyl, isobutyl, t-butyl, cyclohexyl, allyl, benzyl, phenyl, chlorophenyl, xylyl, pyridyl, furanyl, acetyl, benzoyl, butyryl, terephthaloyl. |
| 1 | O | ethoxy, benzyloxy, thioacetoxy, phenoxy, carboethoxy, carbobenzyloxy. |
| | N | ethylamino, diethylamino, propylamido, benzylamino, benzoylamido, phenylacetamido. |
| | S | thiobutyl, thioisobutyl, thioallyl, thiobenzyl, thiophenyl, thiopropionyl, phenylthioacetyl, thiobenzoyl. |
| | SO | butylsulfoxy, allysulfoxy, benzylsulfoxy, phenylsulfoxy. |
| | SO$_2$ | butylsulfonyl, allysulfonyl, benzylsulfonyl, phenylsulfonyl. |
| | P | diethylphosphinyl, ethylvinylphosphinyl, ethylallylphosphinyl, ethylbenzylphosphinyl, ethylpehnylphosphinyl. |
| | PO | diethylphosphinoxy, ethylvinylphosphinoxy, methylallylphosphinoxy, methylbenzylphosphinoxy, methylphenylphosphinoxy. |
| | Si | trimethylsilyl, dimethylbutylsilyl, dimethylbenzylsilyl, dimethylvinylsilyl, dimethylallylsilyl. |

Preferably, the antibacterial enhancing agent is a natural or synthetic anionic polymeric polycarboxylate having a molecular weight of about 1,000 to about 1,000,000, preferably about 30,000 to about 500,000.

The synthetic anionic polymeric polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, as Gantrez, e.g. AN 139 (M.W. 500,000), AN 119 (M.W. 250,000); and preferably S-97 Pharmaceutical Grade (M.W. 70,000), of GAF Corporation.

Other polymeric polycarboxylates containing or modified to contain retention enhancing groups operative in the practice of the present invention include the 1:1 copolymers of maleic anhydride with ethyl acrylate, hydroxyethyl, methacrylate, N-vinyl-2-pyrollidone, or ethylene, the latter being available, for example, as Monsanto EMA No. 1103, M.W. 10,000 and EMA Grade 61, and 1:1 copolymers of acrylic acid with methyl or hydroxyethyl methacrylate, methyl or ethyl acrylate, isobutyl, isobutyl vinyl ether or N-vinyl-2-pyrrolidone.

Additional operative polymeric polycarboxylates containing or modified to contain retention enhancing groups include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Also suitable for use in the practice of the present invention are polymerized olefinically or ethylenically unsaturated carboxylic acids containing an activated carbon-to-carbon olefinic double bond which readily functions on polymerization because of its presence in the monomer molecule either in the alpha-beta position with respect to a carboxyl group or a part of a terminal methylene grouping. Illustrative of such acids are acrylic, methacrylic, ethacrylic, alpha-chloroacrylic, crotonic, beta-acryloxy propionic, sorbic, alphachlorsorbic, cinnamic, betastyrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomer copolymerizable with such carboxylic monomers include vinylacetate, vinyl chloride, dimethyl maleate and the like. Copolymers contain sufficient carboxylic salt groups for water-solubility.

Also useful in the practice of the present invention are so-called carboxyvinyl polymers. They are commercially available, for example, under the trademarks Carbopol 934, 940 and 941 of B. F. Goodrich, these products consisting of a colloidally water-soluble polymer of polyacrylic acid crosslinked with from about 0.75% to about 2.0% of polyallyl sucrose or polyallyl pentaerythritol as a cross linking agent.

Illustrative of antibacterial enhancing agents containing phosphionic acid and/or sulfonic acid delivery enhancing groups, are polymers and copolymers containing units or moieties derived from the polymerization of vinyl or allyl phosphinic and/or sulfonic acids substituted as needed on the 1 or 2 or 3 carbon atom by an organic retention-enhancing group, for example having the formula —(X)$_n$—R defined above. Mixtures of these monomers may be employed, and copolymers thereof with one or more inert polymerizable ethylenically unsaturated monomers such as those described above with respect to the operative synthetic anionic polymeric polycarboxylates.

As an example of a polymer containing repeating units in which one or more phosphonic acid delivery-enhancing groups are bonded to one or more carbon atoms in the polymer chain is poly(vinyl phosphonic acid) containing units of the formula:

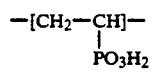     I which however does not contain a retention-enhancing group. A group of the latter type would however be present in poly (1-phosphonopropene) with units of the formula:

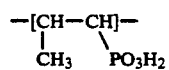     II

A preferred phosphonic acid-containing polymer for use herein is poly (beta styrene phosphonic acid) containing units of the formula:

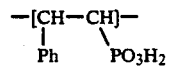     III wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of formula III alternating or in random association with units of formula I above, or poly(alpha styrene phosphonic acid) containing units of the formula:

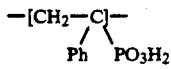  IV in which the delivery-and retention-enhancing groups are terminally bonded to the chain.

These styrene phosphonic acid polymers and their copolymers with other inert ethylenically unsaturated monomers generally have molecular weights in the range of about 2,000 to about 30,000, preferably about 2,500 to about 10,000.

Other phosphonic-containing polymers include, for example, phosphonated ethylene having units of the formula:

  V where n may for example be an integer or have a value giving the polymer a molecular weight of about 3,000; and sodium poly (butene-4,4-diphosphonate) having units of the formula:

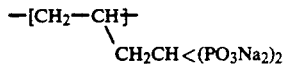

and poly(allyl bis (phosphonoethyl) amine) having units of the formula:

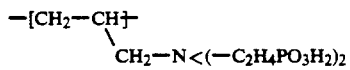  VI

Other phosphonated polymers, for example poly (allyl phosphono acetate), phosphonated polymethacrylate, etc. and the geminal diphosphonate polymers disclosed in EP Publication 0321233 are also useful in the practice of the present invention provided that they contain or are modified to contain the above-defined organic retention-enhancing groups.

Polysiloxanes containing or modified to contain pendant delivery-enhancing groups and retention enhancing groups such as liquid silicone oils such as diphenyl or di ($C_1$–$C_4$) alkyl polysiloxanes and particularly dimethylpolysiloxane, may also be employed in the practice of the present invention.

Also effective herein are ionomers containing or modified to contain delivery-and-retention-enhancing groups. Ionomers are described on pages 546–573 of the Kirk Othmer Encyclopedia of Chemical Technology, third edition, Supplement Volume, John Wiley & Sons, Inc. copyright 1984, which description is incorporated herein by reference. Also effective herein, provided they contain or are modified to contain retention-enhancing groups, are polyesters, polyurethanes and synthetic and natural polyamides including proteins and proteinaceous materials such as collagen, poly (arginine) and other polymerized amino acids.

The antibacterial enhancing agent is incorporated in the compositions of the present invention in weight amounts of about 0.05 to about 5%, and preferably about 0.1 to about 3%.

The oral composition of the present invention may be a solution of ingredients such as a mouthrinse or it may be semi-solid such as a toothpaste or substantially gel in character, such as a gel dentifrice and may contain 0–75% be weight of a polishing agent.

Oral gel preparations contain a siliceous polishing material including crystalline silica having particle sizes of up to about 5 microns, silica gel and colloidal silica and complex amorphous alkali metal aluminosilicate.

When visually clear or opacified gels are employed, a polishing agent of colloidal silica, such as those sold under the trademark Sylox as Silox 15, or under the trademark Syloid as Syloid 72 and Syloid 74, or under the trademark Santocel as Santocel 100, or under the trademark Zeodent as Zeodent 113 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrices.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol typically total about 20–75% by weight of the oral composition, more typically about 25–60%.

When the oral composition is substantially semi-solid or pasty in character, such as a toothpaste (dental cream), the vehicle of the dentifrice contains a polishing material such as sodium bicarbonate, sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, silica, bentonite, and mixtures thereof with each other or with hard polishing materials such as calcined alumina and zirconium silicate. Preferred polishing materials include insoluble sodium metaphosphates, dicalcium phosphate, calcium pyrophosphate and hydrated alumina.

The polishing material is generally present in the cream or paste compositions in weight concentrations of about 30% to about 75%.

Toothpastes or dental cream dentifrices as well as gel dentifrices typically contain a natural or synthetic thickener or gelling agent in proportions of about 0.1 to about 10%, preferably about 0.5 to about 5%.

Suitable thickeners or gelling agents include Irish moss, iotacarrageenan, gum tragacanth, starch, polyvinylpyrrolidone, hydroxyethylpropyl-cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or propylene glycol may be present in amount of about 10-30% by weight. Mouthrinses typically contain about 50-85% of water, about 0 to 20% by weight of a non-toxic alcohol and about 10-40% by weight of the humectant.

The oral composition of the present invention may also contain a source of fluoride ions or fluorine-providing component, as anticaries agent in amount sufficient to supply about 25 ppm to 5000 ppm of fluoride ions. These compounds may be slightly soluble in water or may be fully water-soluble. They are characterized by their ability to release fluoride ions in water and by substantial freedom from undesired reaction with other compounds of the oral composition. Among these materials are inorganic fluoride salts, such as soluble alkali metal, alkaline earth metal salts, for example, sodium fluoride, potassium fluoride, ammonium fluoride, calcium fluoride, a cuprous fluoride, zinc fluoride, barium fluoride, sodium monofluorophosphate, aluminum mon-o and di-fluorophosphate and sodium calcium pyrophosphate. Alkali metal and tin fluorides, such as soduim and stannous fluorides, sodium monofluorophosphate (MFP) and mixtures thereof, are preferred.

The amount of fluorine-providing compound is dependent to some extent upon the type of compound, its solubility, and the type of oral composition, but it must be a non-toxic amount, generally about 0.0005 to about 3.0% in the preparation. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the composition, and preferably in the amount of about 0.05% to 1%. In the case of sodium monofluorophosphate, the compound may be present in an amount of about 0.1-3%, more typically about 0.76% by weight.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucros, lactose, maltose, xylitol, sodium cyclamate, perillartine, aspartyl phenyl alanine methyl ester, saccharine and the like. Suitably, flavor and sweetening agents may each or together comprise from about 0.1% to 5% more of the preparation.

Agents used to diminish teeth sensitivity such as strontium chloride, potassium nitrate and potassium citrate can also be included in the oral compositions of the present invention at concentrations of about 0.1 about 10% by weight.

Various other materials may be incorporated in the oral compositions of this invention such as whitening agents such as urea peroxide and hydrogen peroxide, densensitizing agents such as potassium nitrate, preservatives, such as sodium benzoate, chlorophyll compounds and/or ammoniated material such as urea, diammonium phosphate, and mixtures thereof. These adjuvants, when present, are incorporated in the compositions in amounts which do not substantially adversely affect the properties and characteristics desired.

The dentifrice composition of the present invention may be prepared by suitably mixing the ingredients. For instance, in the preparation of a mouthrinse, the salicylanilide compound is dispersed in a mixture of alcohol humectants, surfactants, and antibacterial enhancing agent and salts such as sodium fluoride and potassium phosphate, and flavor are then added and mixed. The ingredients are then mixed under vacuum for about 15-30 minutes. The resulting rinse is then packaged.

The following examples are further illustrative of the nature of the present invention, but it is understood that the invention is not limited thereto. All amounts and proportions referred to herein and in the appended claims are by weight, unless otherwise indicated.

EXAMPLE 1

A mouthrinse using 5-n-octanoyl-3-trifluromethyl salicylanilide (hereinafter designated "Fluro Salicylanilide" or FS) having the following formula was prepared.

| Ingredient | % by weight |
| --- | --- |
| Ethanol | 15.0 |
| Polyethylene Glycol 600 | 5.0 |
| Propylene Glycol | 15.0 |
| Fluro Salicylanilide | 0.05 |
| Sodium lauryl Sulfate (SLS) | 0.25 |
| Pluronic F127 (Pluronic) | 0.25 |
| Tauranol | 0.25 |
| $K_2HPO_4$ | 0.125 |
| Flavor | 0.10 |
| Water (irradiated) | Q.S. |

The pH of the mouthrinse was adjusted to 8.6 with KOH.

The mouthwash was bottled and stored. The clarity and stability of the mouthrinse was determined by observing the bottle contents after being stored at ambient room temperature for 7 days.

The bottle contents after this storage period were found to be clear and no separation of the contents was noted. For purposes of comparison, the procedure of Example I was repeated except either the concentration of the surfactant ingredients of the mouthrinse were varied or substituted in whole or in part by Tween 20, (trademark) polyoxyethylene (20) sorbitan monolaurate, a non-ionic surfactant available from I.C.I. Americas. The results of the clarity and stability tests are summarized in Table I below.

TABLE I

Clarity and Stability of Comparative Mouthrinses Containing Fluro Salicylanilide

| Mouth-rinse No. | Surfactant (Wt %) | | | | | Solubility Stability |
| --- | --- | --- | --- | --- | --- | --- |
| | FS | SLS | Pluronic | Tauranol | Tween* | |
| $C_1$ | 0.05 | 0.25 | — | — | — | Opaque, Separates, Unstable |
| $C_2$ | 0.05 | 0.25 | — | 0.25 | — | Clear, Separates, Unstable |
| $C_3$ | 0.05 | 0.25 | 0.25 | — | — | Clear, Separates, Unstable |
| $C_4$ | 0.05 | 0.25 | — | — | 0.50 | Clear, Stable |
| $C_5$ | 0.05 | 0.25 | — | — | 0.75 | Clear, Stable |
| $C_6$ | 0.05 | 0.25 | — | — | 1.00 | Clear, Stable |
| $C_7$ | 0.05 | — | — | — | 1.50 | Clear Stable |

*Designation for Tween 20.

The data recorded in Table I indicates that mouthrinses formulated with 5-n-octanoyl-3'-trifluromethyl salicylanilide ("FS") are unstable when the surfactant system is SLS as the sole surfactant, ($C_1$) or the combination, SLS/Pluronic ($C_3$) or SLS/Tauranol, ($C_2$). The mouthrinses are clear and stable when Tween 20 is used alone or in combination with SLS ($C_4$–$C_7$).

EXAMPLE II

The antibacterial activity of the clear, stable salicylanilide mouth rinse composition prepared in Example I as well as the clear, stable comparative rinse compositions $C_4$–$C_7$ were evaluated for antibacterial efficacy in vitro against A. viscosus and S. mutans, two microorganisms present in human plaque, by the short interval killing test (SIKT) method.

The SIKT test is an in vitro antimicrobial test which incorporates a fixed contact time wherein 1 ml of mouthrinse is mixed with a pre-determined inoculum of A.viscosus ($10^6$–$10^7$) colony forming unit, (cfu/ml) for a 1-2 minutes contact time. The system is then neutralized to inhibit further antibacterial activity. This procedure simulates human mouthrinse condition. The surviving bacteria are enumerated using plate count methodology. The reduction in cfu counts compared to a water control is the basis for expressing antibacterial activity of the agents. The results of the SIKT test are recorded in Table II below.

TABLE II

SKIT Antibacterial Activity of Stable Fluro Salicylanilide Mouthrinses Against A. viscosus

| Rinse No. | Surfactant wt % | | | | | cfu × $10^5$/ml | SKIT (% kill) |
|---|---|---|---|---|---|---|---|
| | FS | SLS | Pluronic | Tauranol | Tween | | |
| 1 | 0.05 | 0.25 | 0.25 | 0.25 | — | 1.7 | 99.7 |
| $C_4$ | 0.05 | 0.25 | — | — | 0.50 | 95.0 | 27.2 |
| $C_5$ | 0.05 | 0.25 | — | — | 0.75 | 130.5 | 0.0 |
| $C_6$ | 0.05 | 0.25 | — | — | 1.00 | 107.0 | 17.9 |
| $C_7$ | 0.05 | — | — | — | 1.50 | 110.5 | 15.4 |
| Control | Water | — | — | — | — | 130.5 | 0.0 |

The SIKT test results recorded in Table II indicate that the antibacterial efficacy of the mouthrinse of the present invention containing 5-n-octanoyl-3'-trifluromethyl salicylanilide and a SLS/Pluronic/Tauranol surfactant system is quite strong (99.7% kill) against A. viscosus, a plaque microorganism, especially when compared to the same salicylanilide compound containing rinse in which the surfactant system is absent from the rinse or substituted for by a SLS/Tween 20, system (Rinse nos. $C_4$–$C_7$) wherein the antibacterial activity is minimal (15–18% kill, Rinse Nos. $C_4$, $C_6$–$C_7$) or there is no activity at all (Rinse No. $C_5$).

EXAMPLE III

The minimum inhibitory concentration (MIC) of the rinse composition of Example I was determined in vitro against A. viscosus and S. mutans. MIC is a measure of the efficacy of the antibacterial agent in vitro. MIC is defined as the minimum inhibition concentration in parts per million (ppm) of the antibacterial agent at which the growth of bacteria is completely inhibited by the agent. The smaller the MIC value, the greater is the efficacy of the antibacterial agent to inhibit the growth of the bacteria. The in vitro MIC data is related to the efficacy of the dentifrice in vivo since retention and release of the antibacterial agent into the oral cavity after toothbrushing or rinsing is in the ppm range. The MIC of the rinse composition of Example I is recorded in Table III below.

For purposes of comparison, mouthrinses were prepared in accordance with the procedure of Example I wherein the surfactant system SLS/Tauranol was used instead of SLS/Pluronic/Tauranol (Ca) or no salicylanilide compound was included in the mouthrinse formulation (Rinse No. $C_{10}$). The MIC results of these comparative mouthrinses are also recorded in Table III are recorded in Table III below.

TABLE III

Antibacterial Activity (MIC) of Salicylanilide Rinse

| Rinse No. | Wt % | | Surfactant (Wt %) | | Antibacterial Activity (MIC, ppm) | |
|---|---|---|---|---|---|---|
| | FS | SLS | Pluronic | Tauranol | A. viscosus | S. mutans |
| Ex. 1 | 0.25 | 0.25 | 0.25 | 0.25 | 0.32 | 0.32 |
| $C_9$ | 0.25 | 0.25 | — | 0.25 | 1.25 | — |
| $C_{10}$ | — | 0.25 | 0.25 | 0.25 | >5.0 | >5.0 |
| Control | 0.25 | Methanol | — | — | 1.25 | 1.25 |

The results of the MIC study recorded in Table III indicate that the salicylanilide rinse of the present invention showed strong antibacterial activity against two test plaque microorganisms whereas salicylanilide containing rinses formulated with a surfactant system in which Pluronic F127 was absent ($C_9$), or the salicylanilide compound was absent from the rinse ($C_{10}$), exhibited minimal antibacterial activity. The results further show that the salicylanilide rinse provided antibacterial activity well above that obtained with a rinse based on the salicylanilide compound being incorporated in a simple solvent system such as methanol (Control).

EXAMPLE IV

The effect in vitro of a synthetic anionic linear polycarboxylate (Gantrez S-97) on the salicylanilide uptake on tooth surfaces of salicylanilide containing mouthrinses was assessed using a saliva coated hydroxyapatite disk. The in vitro assessment is correlatable to in vivo delivery and retention on oral surfaces. The composition of the mouthrinse is summarized in Table IV below. For purposes of comparison, a similar mouthrinse was prepared without the inclusion of Gantrez S97 (composition B).

In this test of uptake of salicylanilide antibacterial agent to a saliva coated hydroxyapatite disk, hydroxyapatite (HAP) obtained from the Monsanto Co. was washed extensively with distilled water, collected by vacuum filtration and permitted to dry overnight at 37° C. The dried HAP was ground into a powder with a mortar and pestle. 150 mgs of HAP were placed in the chamber of a KBr pellet die (Barnes Analytical Stanford, Conn.) and compressed for 6 minutes at 10,000 pound in a Carver Laboratory press. The resulting 13 mm disks were sintered for 4 hours at 800° C. in a Thermolyne furnace. Parafilm stimulated whole saliva was collected into an ice-chilled glass beaker and then clarified by centrifugation at 15,000 Xg (times gravity) for 15 minutes at 4° C. Sterilization of the clarified-saliva was done at 4° C. with stirring by irradiation of the sample with UV light for 1.0 hour.

Each sintered test disk was hydrated with sterile water in a polyethylene test tube. The water was then removed and replaced with 2.0 ml of saliva. A salivary pellicle was formed by incubating the disk overnight at 37° C. with continuous shaking in a water bath. After this treatment, the saliva was removed and the disks treated with 1.0 ml of salicylanilide dentifrice solutions A and B and incubated at 37° C. with continuous shaking in the water bath. After 30 minutes, the disks were transferred into a new tube and 5.0 ml of water was added followed by shaking the disks gently with a Vortex. The disks were then transferred into a tube to avoid co-transfer of any liquid along with the disks. Then 1.0 ml of methanol was added to the disks and shaken vigorously with a Vortex. The samples were left at room temperature for 30 minutes to extract absorbed salicylanilide compound into the methanol. The methanol was then aspirated and clarified by centrigugation in a Beckman Microfuge at 10,000 rpm for 5 minutes. After this treatment, the methanol was transferred into HPLC (high performance liquid chromatography) vials for determination of salicylanilide compound. Triplicate samples were used for both compositions.

The uptake results are recorded in Table V below:

TABLE IV

| Compositions of Dentifrice Liquid Phase Solutions* | | |
|---|---|---|
| Solution Ingredients | A gms | B gms |
| Propylene Glycol | 10.0 | 10.0 |
| Sorbitol | 10.0 | 10.0 |
| Glycerol | 10.0 | 10.0 |
| PEG 600 | 5.0 | 5.0 |
| SLS | 0.5 | 0.5 |
| Tauranol | 0.5 | 0.5 |
| Pluronic F127 | 0.5 | 0.5 |
| Sodium Fluoride | 0.243 | 0.243 |
| Gantrez S97 (14.0%)** | 14.28 | 0.0 |
| Fluro Salicylanilide | 0.3 | 0.3 |
| F$_2$HPO$_4$ | 0.5 | 0.5 |
| KOH (25%) | 4.2 | 0.082 |
| Flavor Oil | 1.0 | 1.0 |
| DD-Water | 17.59 | 36.0 |
| Total | 74.62 | 74.62 |

*pH = 8.6
**anionic polymeric polycarboxylate

TABLE V

| Uptake of Salicylanilide on Saliva Coated HAP Disk | | | | |
|---|---|---|---|---|
| Solution | FS % | Gantrez % | SF Uptake ug/Disk; n = 2 | Increase (%) |
| B | 0.4 | 0.0 | 34.03 +/− 0.78 | — |
| A | 0.4 | 2.0 | 51.75 +/− 2.4 | 52.00 |

The results in Table V show that 2.0% Gantrez (composition A) in dentifrice liquid phase solution enhances the uptake of the Fluor Salicylanilide compound from dentifrice liquid phase solution to a saliva coated HAP disk by 52.00% when compared to the sample containing no Gantrez (sample B).

EXAMPLE V

A series of Fluro salicylanilide containing dentrifrice liquid phase solutions formulated with varying concentrations of Gantrez S97 was prepared having the compositions shown in Table VI

TABLE VI

| Compositions of Dentifrice Liquid Phase Solutions* | | | | | |
|---|---|---|---|---|---|
| Ingredients | A gms | B gms | C gms | D gms | E gms |
| Propylene Glycol | 10.0 | 10.0 | 10.0 | 10.0 | 10.0 |
| Sorbitol | 10.0 | 10.0 | 10.0 | 10.0 | 10.0 |
| Glycerol | 10.0 | 10.0 | 10.0 | 10.0 | 10.0 |
| PEG 600 | 5.0 | 5.0 | 5.0 | 5.0 | 5.0 |
| SLS | 0.5 | 0.5 | 0.5 | 0.5 | 0.5 |
| Tauranol | 0.5 | 0.5 | 0.5 | 0.5 | 0.5 |
| Pluronic F127 | 0.5 | 0.5 | 0.5 | 0.5 | 0.5 |
| Sodium Fluoride | 0.243 | 0.243 | 0.243 | 0.243 | 0.243 |
| Gantrez S97 (14.0%) | 0.0 | 3.57 | 7.14 | 14.28 | 0.0 |
| K$_2$HPO$_4$ | 0.5 | 0.5 | 0.5 | 0.5 | 0.5 |
| KOH (25%) | 0.082 | 1.4 | 2.65 | 4.2 | 0.082 |
| Fluro Salicylanilide | 0.3 | 0.3 | 0.3 | 0.3 | 0.0 |
| Flavor Oil | 1.0 | 1.0 | 1.0 | 1.0 | 1.0 |
| DD-Water | 36.0 | 31.12 | 26.29 | 17.59 | 36.3 |
| Total | 74.62 | 74.62 | 74.62 | 74.62 | 74.62 |

*pH = 8.6

The antiplaque activity of liquid dentifrices (A,B,C,D and E) of Table VI was assessed using a chemostat plaque model system of the type disclosed in the American Journal of Dentistry, Vol. 3, pages S8–S9 (1990). The chemostat consisted of a source of bacterial growth media contained in a mixing chamber and flow cells connected thereto. HAP disks prepared in accordance with the procedure of Example IV on which plaque was to be formed were fixed in the flow cells.

A mixed culture of five species of oral microorganisms (A.viscosus, S.mutans, S.sanguis, V.parvula, F.nucleatum) assoicated with human plaque was maintained in the chemostat, and the mixture was then pumped through flow cells at the rate of 1 ml/minute for 48 hours to grow plaque on the HAP disks.

To evaluate the antiplaque efficacy of the liquid dentifrices, the dentifrices were pumped for 30 seconds at the rate of 6 ml/min. through the flow cells containing the HAP disks on which plaque was grown. Thereafter, bacterial plaque grown on the HAP disks was removed by immersion of the disks in 2 ml solution of 0.1N NaOH in a waterbath at 37° C. with gentle shaking for 15 minutes. The disks were removed from the NaOH solution and the solution was then sonically agitated to disperse the plaque. Turbidity Optical Dentistry (O.D.) of the sonically agitated sample, a measure of plaque growth, was then determined by measuring the absorbance at 610 nm in a spectrophotometer. The results are recorded in Table VII below:

TABLE VII

| Effect of Gantrez on Antiplaque Activity of Fluro Salicylanilide Dentifrice Liquid Phase Solutions | | | | |
|---|---|---|---|---|
| Solution | FS wt % | Gantrez wt % | Plaque Growth (O.D.) | Plaque Reduction % |
| E | 0.0 | 0.0 | 0.646 +/− 0.16 | — |
| A | 0.4 | 0.0 | 0.532 +/− 0.07 | 17.6 |
| B | 0.4 | 0.5 | 0.378 +/− 0.05 | 41.5 |
| C | 0.4 | 1.0 | 0.323 +/− 0.06 | 50.0 |
| D | 0.4 | 2.0 | 0.280 +/− 0.08 | 56.6 |

The results, summarized in Table VIII show that solution A containing the fluro salicylanilide compound but no Gantrez reduced in vitro plaque growth by 17.6% when compared to solution E which did not contain the fluro salicylanilide compound or Gantrez. The results further show that Gantrez incorporated in liquid dentifrice solutions B–D containing the fluro salicylanilide compound enhanced antiplaque efficacy of the dentifrice in a dose dependent manner. Liquid dentifrice solution D containing 2% Gantrez enhanced the reduction of plaque growth by 56.6% compared to liquid dentifrice solution E. Solutions B and C containing 0.5% and 1% Gantrez, respectively, also enhanced the inhibition of plaque growth by 41.5% and 50.0%, respectively.

EXAMPLE VI

A series of dentifrice and mouthrinse formulations prepared with and without Gantrez was prepared having the compositions shown in Tables VIII and IX below:

TABLE VIII

| Fluro Salicylanilide Dentifrice Compositions* | | |
|---|---|---|
| Composition | A | B |
| Ingredients | gms | gms |
| Propylene Glycol | 10.0 | 10.0 |
| Sorbitol | 10.0 | 10.0 |
| Glycerol | 10.0 | 10.0 |
| PEG 600 | 5.0 | 5.0 |
| Sodium CMC | 0.8 | 0.8 |
| IOTA** | 0.3 | 0.3 |
| TiO2 | 0.5 | 0.5 |
| SLS | 0.5 | 0.5 |
| Tauranol | 0.5 | 0.5 |
| Pluronic 127 | 0.5 | 0.5 |
| Sodium Fluoride | 0.243 | 0.243 |
| Gantrez S97 (14.0%) | 0.0 | 14.28 |
| K2HPO4 | 0.5 | 0.5 |
| KOH (25%) | 0.082 | 4.2 |
| Saccharin | 0.2 | 0.2 |
| Zeodent 113 | 20.0 | 20.0 |
| Sylox 15 | 2.0 | 2.0 |
| Fluro Salicylanilide | 0.3 | 0.3 |
| Flavor Oil | 1.0 | 1.0 |
| DD-Water | 37.57 | 19.17 |
| Total | 100.00 | 100.00 |

*pH = 8.6
**iota carrageenan

TABLE IX

| Fluro Salicylanilide Mouthrinse* | | | |
|---|---|---|---|
| Ingredients | D % | E % | F % |
| Sorbitol | 10.0 | 10.0 | 10.0 |
| Glycerine | 10.0 | 10.0 | 10.0 |
| Ethanol | 15.0 | 15.0 | 15.0 |
| Propylene Glycol | 15.0 | 15.0 | 15.0 |
| SLS | 0.25 | 0.25 | 0.0 |
| Tauranol | 0.25 | 0.25 | 0.0 |
| Pluronic F127 | 0.25 | 0.25 | 0.25 |
| Flavor Oil | 0.1 | 0.1 | 0.1 |
| Fluro Salicylanilide | 0.04 | 0.04 | 0.0 |
| Gantrez S97 (14%) | 0.0 | 1.42 | 0.0 |
| K2HPO4 (25%) | 0.1 | 0.1 | 0.1 |
| KOH (10%) | 0.2 | 0.45 | 0.2 |
| Water | 48.81 | 47.140 | 49.35 |
| Total | 100.00 | 100.00 | 100.00 |

*pH = 8.6

The antiplaque activity of the dentifrice and mouthrinse compositions was assessed using the chemostat plaque model system following the procedure of Example V. The results are recorded in Tables X and XI below:

TABLE X

| Effect of Gantrez on Antiplaque Activity of FS Dentifrice | | | |
|---|---|---|---|
| Samples | FS % | Gantrez % | Plaque Growth (O.D.) | Plaque Reduction % |
| A | 0.04 | 0.0 | 0.599 +/− 0.14 | — |
| B | 0.04 | 2.0 | 0.414 +/− 0.11 | 30.9 |

TABLE XI

| Effect of Gantrez on Antiplaque Activity of FS Mouthrinse | | | |
|---|---|---|---|
| Samples | FS % | Gantrez % | Plaque Growth (O.D.) | Plaque Reduction* % |
| F | 0.0 | 0.0 | 0.646 +/− 0.16 | — |
| D | 0.04 | 0.0 | 0.551 +/− .07 | 14.7 |
| E | 0.04 | 0.2 | 0.378 +/− 0.05 | 41.5 |

The results in Table X show that the salicylanilide dentifrice containing 2% Gantrez (B), enhanced the inhibition of plaque growth by 30.9% compared to salicylanilide dentifrice containing no Gantrez (A).

The results in Table XI show that the fluro salicylanilide mouthrinse containing 0.2% Gantrez (E) enhances the inhibition of plaque growth by 41.5% compared to placebo mouthrinse F containing no fluro salicylanilide or Gantrez. On the otherhand, salicylanilide mouthrinse D containing no Gantrez reduced plaque growth by 14.7% compared to placebo rinse F.

What is claimed is:

1. An oral composition for inhibiting plaque on teeth comprising a vehicle in which is incorporated an antiplaque system of (a) an effective antibacterial amount of a salicylanilide compound and (b) a surfactant mixture of an anionic surfactant, a polyoxyethylene-polyoxypropylene block copolymer and a taurate salt, the pH of the composition being about 8.0 to 11.0.

2. The oral composition of claim 1 wherein the salicylanilide compound is a halogenated salicylanilide.

3. The oral composition of claim 2 wherein the halogenated salicylanilide is a fluorinated 5-acyl salicylanilide.

4. The oral composition of claim 3 wherein the fluorinated 5-acyl salicylanilide as 5-n-octanoly-3'-trifluormethyl salicylanilide.

5. The oral composition of claim 1, wherein the salicylanilide compound is incorporated in the composition at a concentration of about 0.01 to about 2.0% by weight.

6. The oral composition of claim 1 wherein the anionic surfactant is sodium lauryl sulfate.

7. The oral composition of claim 1 wherein the polyoxyethylene-polypropylene block copolymer is a block copolymer containing about 10-80% by weight polyoxyethylene groups and has a molecular weight from about 3000 to about 5000.

8. The oral composition of claim 1 wherein the taurate salt is an alkali metal taurate.

9. The oral composition of claim 8 wherein the alkali metal taurate is sodium methyl cocoyl taurate.

10. The oral composition of claim 1 wherein the surfactant mixture is incorporated in the composition at a concentration of about 0.30 to about 3.0% by weight.

11. The oral composition of claim 10 wherein the surfactant mixture is present in the composition at a weight ratio of about 1:1:1.

12. The oral composition of claim 1 wherein an antibacterial enhancing agent is included in the composition.

13. The oral composition of claim 12 wherein the antibacterial enhancing agent is an anionic polymeric polycarboxylate.

14. The oral composition of claim 13 wherein the anionic polymeric polycarboxylate is a methyl vinyl ether/maleic anhydride copolymer.

15. The oral composition of claim 12 wherein the antibacterial enhancing agent is incorporated in the composition at a concentration of about 0.05 to about 5% by weight.

16. A method for inhibiting plaque on teeth comprising applying to said teeth an oral composition comprising a vehicle in which is incorporated (a) an antiplaque system of an effective antibacterial amount of a salicylanilide compound and (b) a surfactant mixture of anionic surfactant, polyoxyethylenepolypropylene block copolymer and taurate salt wherein the pH of the oral composition is about 8.0 to 11.0.

17. The method of claim 16 wherein the salicylanilide compound is a halogenated salicylanilide.

18. The method of claim 17 wherein the halogenated salicylanilide is a fluorinated 5-acyl salicylanilide.

19. The method of claim 18 wherein the fluorinated 5-acyl salicylanilide is 5-n-octanoyl-3'-trifluormethyl salicylanilide.

20. The method of claim 1 wherein the salicylanilide compound is incorporated in the composition at a concentration of about 0.01 to about 2.0% by weight.

21. The method of claim 16 wherein the anionic surfactant is sodium lauryl sulfate.

22. The method of claim 16 wherein the polyoxyethylene-polypropylene block copolymer is a block copolymer containing about 10–80% by weight polyoxyethylene groups and has a molecular weight from about 3000 to about 5000.

23. The method of claim 16 wherein the taurate salt is an akali metal taurate.

24. The method of claim 23 wherein the alkali metal taurate is sodium methyl cocoyl taurate.

25. The method of claim 16 wherein the surfactant mixture is incorporated in the composition at a concentration of about 0.2 to about 3.0% by weight.

26. The method of claim 25 wherein the surfactant mixture is present in the composition at a weight ratio of about 1:1:1.

27. The method of claim 16 wherein an antibacterial enhancing agent is included in the composition.

28. The method of claim 27 wherein the antibacterial enhancing agent is a synthetic anionic polymeric polycarboxylate.

29. The method of claim 28 wherein the anionic polymeric poycarboxylate is a methyl vinyl ether/maleic anhydride copolymer.

30. The method of claim 28 wherein the antibacterial enhancing agent is incorporated in the composition at a concentration of about 0.05 to about 5% by weight.

* * * * *